(12) United States Patent
Gunday et al.

(10) Patent No.: US 8,864,762 B2
(45) Date of Patent: Oct. 21, 2014

(54) BALLOON CATHETER MESH

(75) Inventors: Erhan H. Gunday, Great Neck, NY (US); Lawrence J. Gerrans, San Anselmo, CA (US)

(73) Assignee: Sanovas, Inc., San Rafael, CA (US)

( * ) Notice: Subject to any disclaimer, the term of this patent is extended or adjusted under 35 U.S.C. 154(b) by 830 days.

(21) Appl. No.: 13/107,426

(22) Filed: May 13, 2011

(65) Prior Publication Data

US 2012/0289982 A1 Nov. 15, 2012

(51) Int. Cl.
| | | |
|---|---|---|
| *A61B 18/12* | (2006.01) | |
| *A61B 18/14* | (2006.01) | |
| *A61B 17/3207* | (2006.01) | |
| *A61B 17/00* | (2006.01) | |
| *A61M 25/10* | (2013.01) | |
| *A61B 19/00* | (2006.01) | |
| *A61B 17/22* | (2006.01) | |
| *A61B 18/02* | (2006.01) | |

(52) U.S. Cl.
CPC ............. *A61B 17/320725* (2013.01); *A61B 2017/00026* (2013.01); *A61M 2025/109* (2013.01); *A61M 2025/105* (2013.01); *A61B 2019/448* (2013.01); *A61M 2025/1081* (2013.01); *A61B 2218/002* (2013.01); *A61B 2017/22051* (2013.01); *A61M 2025/1086* (2013.01); *A61B 18/1492* (2013.01); *A61M 2025/1079* (2013.01); *A61B 18/02* (2013.01); *A61M 25/10* (2013.01)
USPC ................................ 606/45; 606/41; 606/159

(58) Field of Classification Search
CPC .... A61B 18/12; A61B 18/14; A61B 18/1492; A61B 2218/002; A61B 2018/0016; A61B 2018/00214; A61B 2018/0022; A61B 2018/00345; A61B 2018/00571; A61B 2018/00875; A61B 2018/00244; A61B 25/10; A61B 2025/105; A61B 2025/1079; A61B 2025/1081; A61B 2025/1086; A61B 2025/109
USPC ........................................ 606/27, 34, 41, 159
See application file for complete search history.

(56) References Cited

U.S. PATENT DOCUMENTS

| | | | | |
|---|---|---|---|---|
| 4,885,003 | A * | 12/1989 | Hillstead ........................ | 604/22 |
| 5,150,717 | A * | 9/1992 | Rosen et al. .................. | 607/156 |
| 5,226,430 | A * | 7/1993 | Spears et al. .................. | 128/898 |
| 5,743,905 | A * | 4/1998 | Eder et al. ...................... | 606/32 |
| 7,137,980 | B2 * | 11/2006 | Buysse et al. ................... | 606/34 |
| 2006/0004353 | A1 * | 1/2006 | Koyfman et al. .............. | 606/41 |
| 2007/0083192 | A1 * | 4/2007 | Welch ............................ | 606/41 |
| 2007/0118112 | A1 * | 5/2007 | Kennedy, II ................... | 606/45 |
| 2010/0121270 | A1 | 5/2010 | Gunday et al. | |

FOREIGN PATENT DOCUMENTS

EP 1913882 A1 4/2008

* cited by examiner

*Primary Examiner* — Michael Peffley
*Assistant Examiner* — Daniel Fowler
(74) *Attorney, Agent, or Firm* — St. Onge Steward Johnston & Rees LLC

(57) ABSTRACT

A resector balloon includes an outer wall having a resecting surface that resects biological material. The balloon also includes a woven sleeve including at least one woven thread disposed on at least a portion of the outer wall. The woven sleeve forms at least a portion of the resecting surface. In certain embodiments, the woven sleeve includes weft knit threads including crossover points where the threads overlap. In some embodiments, the woven sleeve includes electrically conductive threads.

47 Claims, 13 Drawing Sheets

BALLOON CATHETER MESH

TECHNICAL FIELD

The apparatus described herein generally relates to the field of resecting unwanted biological material, such as tissue growths and tumors, in body cavities, providing a non-slip surface, and providing a radio opaque surface for imaging and biopsy. More specifically, the apparatus relates to a woven mesh for the resecting surface of a balloon catheter.

BACKGROUND

The removal of unwanted and/or life threatening biological material from interior portions of bodily cavities, such as organs, vessels, articular joints and structures, sinuses, and various bodily lumens, is a very common procedure in various medical specialties and disciplines, such as pulmonology, cardiology, urology, gynecology, gastro-enterology, neurology, otolaryngology, orthopedics, and general surgery. Accordingly, various instruments and methods have been employed to perform these procedures, which are generally well known in the art.

One of the most important complications in such procedures is bleeding. The bleeding and resulting morbidity of tissue that occurs in many of the currently known surgical procedures is the result of abrasive, traumatic, and invasive excising and removal techniques. Many of these techniques risk perforation of the vessel or lumen in which the procedure is being performed, resulting in grave complications for the surgeon and patient. In addition, many patient maladies are simply not remedied by these procedures because no interventional, minimally invasive treatment modality exists, the methods are not efficient, safe, and reproducible, and/or the instruments employed lack the appropriate visualization, physiological measurement, and/or feedback necessary to ensure the safety, efficacy, and reproducibility of the procedure. Accordingly, a new type of treatment is required.

One instrument that is commonly used in various types of medical procedures is an inflatable balloon catheter. One particular application of such catheters is lung cancer. Among all types of cancer, this has the lowest survival rate, as more than one third of all deaths due to cancer are caused by lung cancer. Over 1.5 million new cases are diagnosed worldwide each year. The most frequent cause of death for lung cancer patients is airway obstruction. In lung cancer patients, one third of all cases initially, and another third of the cases in the long term, present main airway obstruction, which may cause asphyxia, hemorrhaging, and infection. These complications are the most frequent causes of death in lung cancer patients.

Use of interventional bronchoscopy for the treatment of lung cancer and the resultant airway obstruction increases the quality of life and survival rates of patients suffering from Chronic Obstructive Pulmonary Disease (COPD) and the obstructive co-morbidities associated with the cancer. Accordingly, balloon catheters have been routinely used with various endoscopes and with flexible and rigid bronchoscopes for dilation, as a tamponade to stop bleeding, and as an interference fixation device to hold instruments in place and prevent the retropulsion of those instruments under backflow pressure.

In light of the aforementioned need for a new type of treatment for removing undesirable biological material in bodily cavities, it has been realized that inflatable balloon catheters may further be employed as interventional tools for the excision and removal of such materials—such as endoluminal obstructions and tumors and endovascular occlusions—in various applications, such as the aforementioned interventional medical specialties of pulmonology, cardiology, urology, gynecology, gastro-enterology, neurology, otolaryngology, and general surgery. The use of balloon catheters in this way has presented a method of treatment that is simple, safe, highly effective, and inexpensive compared to other types of methods and devices that are used, such as mechanical, laser, electrocautery, cryotherapy, etc.

Accordingly, a new class of balloons has been suggested for this purpose, such as that disclosed in European Patent Application No. EP 1 913 882 by Karakoca. This device employs a balloon catheter with a hardening surface, which can be inserted into bodily cavities. After the device is inserted, the balloon is inflated, and the balloon is moved back and forth within the cavity such that the hardened surface performs a shaving action on the unwanted biological material. In this way, the targeted material is resected.

However, this particular instrument and method of using it suffers from a number of disadvantages and shortcomings. One of the most significant problems with this resector balloon is that unwanted biological material is removed by shaving it with the hardened surface on the outside of the balloon—i.e., by moving the balloon back and forth and/or rotating it. This mechanism of action can be abrasive and traumatic. Moreover, the hardened surface coupled with the shaving action can sometimes lack the precision necessary to prevent complications such as bleeding and structural perforation of the affected anatomical structure. Furthermore, the amount of torque and back and forth force needed on the balloon may cause a device failure, particularly where the balloon is attached to the catheter.

Another problem with this resector balloon is that it further lacks accuracy because it lacks the capability to precisely gauge the size of the environment in which it is being used to provide physiological measurements and feedback that could aid treatment intervention and efficacy. For example, there is no way for the surgeon to know the diameter of the affected bodily cavity itself, proximal or distal to the obstruction therein. Similarly, there is no way for the surgeon to know the intra-lumen diameter where the unwanted tissue growth or tumor resides, and further, no way to accurately adjust for changes in this diameter over time as the growth or tumor is resected. Because it has no mechanism for measuring the intra-lumen diameter at different points within the cavity, and particularly, how this changes over time, one is not able to properly adjust the amount of pressure supplied to the balloon and thereby prevent complications and expedite treatment.

A related problem with this device is that there is no way for a physician to measure the intra-articular space between two articular structures, endplates, or surfaces.

Yet another related problem with this device is that there is no way for the surgeon to know the density of the bodily cavity proximal or distal to the obstruction, nor can the surgeon know the density of the growth or tumor itself. Because there is no mechanism for measuring the density of the cavity or the obstruction, one is likewise unable to properly control the pressure in the balloon to aid surgical precision, minimize potential complications, and expedite the procedure.

Another deficiency is the inability to of conventional resector balloons to directly measure the diameter of the balloon and the cavity it is disposed in. Furthermore, conventional resector balloons cannot directly detect the tissue or fluid they are in contact with.

Yet another deficiency is the inability to control the balloon inflation pressure and thus the amount of safe radial force exerted on the lumen walls.

A further deficiency is that conventional resector balloons lack sufficient texture or friction to resect tissue efficiently. Furthermore, conventional resector balloons cannot adjust the amount of texture or friction of their resector surface in vivo or in real time. A further deficiency is the inability of known resector balloons to conveniently sample tissue for lab analysis or biopsy.

Another deficiency of known resector balloons is the inability to efficiently deliver energy to tissue. Energy delivery to tissue can help destroy the tissue or cauterize it to prevent bleeding or unwanted emissions of other biological fluids.

Accordingly, it has been proposed to control a resector balloon using a more advanced system, such as that disclosed in U.S. Patent Application No. 2010/0121270 by Gunday et al., the specification of which is hereby incorporated by reference herein in its entirety. In this type of system, a fluid source is used to inflate and deflate the balloon in pulsed fashion and can be operated according to presets that correspond to the resector balloon installed thereon, which allows for safe, precise resection that will not harm healthy tissue. The system receives operation feedback from the balloon, from which it can make relatively accurate estimations of the dimensions and other material properties of the material surrounding the balloon. Using these estimations, the system can adjust its operating parameters in real time to optimize the resecting procedure.

This type of system can be improved by using additional means of obtaining data about the resector balloon's environment, which can allow for more detailed and precise information about that environment and thereby facilitate improved control and optimization of the balloon's operating parameters, as well as improved feedback to the physician performing the operation.

What is desired, therefore, is a resector balloon system for removing undesirable biological materials that does not cause unnecessary trauma to the affected bodily cavity. What is also desired is a resector balloon system with controllable rates of inflation and deflation. What is also desired is a resector balloon system with independently controllable, conforming balloon geometries. What is also desired is a resector balloon system that is able to provide direct and accurate physiologic feedback to determine intra-lumen diameters and densities where the unwanted biological material resides and at locations proximal, distal and/or lateral to such material, the intra-articular space between two articular structures, and the type of balloon catheter connected. What is further desired is a resector balloon system that can be illuminated and imaged directly and indirectly, via radiopaque markers. What is also desired is a resector balloon system that is able to provide dimensional and performance metrics of the anatomy and the balloon catheter construct in vivo. What is further desired is a resector balloon that can accurately and directly analyze tissue, detect balloon size and relate environmental factors such as temperature, pressure and flow rates. What is further desired is a resector balloon that can deliver energy and sound waves to tissue and enhance or adjust the friction of its resecting surface. What is further desired is a resector balloon that can conveniently extract and retain tissue for sampling/analysis.

BRIEF SUMMARY

Accordingly, it is an object of the present invention to provide a resector balloon system for removing undesirable biological material that does not require a shaving mechanism of action.

It is yet another object of the present invention to provide a resector balloon system for removing undesirable biological material that provides physiological feedback from which the intra-lumen diameter where the material resides, as well as the bodily cavity itself proximal, distal and lateral to the material, can be determined, and the energy, pressure and flow supplied to the balloon can be adjusted accordingly.

It is still another object of the present invention to provide a resector balloon system for removing undesirable biological material that provides physiological feedback and dimensional metrics from which the intra-articular space and articular geometries between two articular structures, endplates, or surfaces can be determined, and the energy, pressure and flow supplied to the balloon can be adjusted accordingly.

It is yet another object of the present invention to provide a resector balloon system for removing undesirable biological material that provides physiological feedback from which the intra-lumen density where the material resides, as well as the bodily cavity itself proximal, distal and lateral to the material, can be determined, and the energy, pressure and flow supplied to the balloon can be adjusted accordingly.

It is another object of the present invention to provide a resector balloon system for removing undesirable biological material that can deliver energy to the target area.

It is still another object of the present invention to provide a resector balloon system for removing undesirable biological material that can provide information about the nature of the biological material to be removed.

It is another object of the present invention to provide a resector balloon system in which the pressures required to inflate the balloon can be predicted and characterized.

It is yet another object of the present invention to provide a resector balloon system that is electrically conductive and/or radio opaque.

It is still another object of the present invention to provide a resector balloon system that enables direct and indirect imaging.

It is yet another object of the present invention to provide a resector balloon system having a balloon surface material that is uniform, having dimensions such us outer diameter, inner diameter, thickness, and elasticity that are consistent.

In order to overcome the deficiencies of the prior art and to achieve at least some of the objects and advantages listed, the invention comprises a resector balloon including an outer wall having a resecting surface that resects biological material. The balloon also includes a woven sleeve including at least one woven thread disposed on at least a portion of the outer wall. The woven sleeve forms at least a portion of the resecting surface.

The woven sleeve may be weft knit. The at least one woven thread may be an elastic string or a polyurethane or nylon string. The at least one woven thread may include metallic fibers or steel fibers. The woven sleeve may include at least one electrically conductive thread. The electrically conductive threads may include an electrically conductive core and an electrically insulative sheath. The electrically conductive threads may include an electrically insulative core and an electrically conductive sheath. A proximal and distal portion of the woven sleeve may include electrically conductive threads while a middle portion of the woven sleeve may include electrically insulative threads. The woven sleeve may comprise yarn coated with electrically conductive material or yarn coated with electrically insulative material. The woven sleeve may comprise yarn that is alternately electrically insulative and conductive along its length. At least part of the woven sleeve may be radio opaque.

The balloon may be coupled to a catheter, and a proximal and distal end of the woven sleeve may be coupled to the catheter. The proximal and distal ends of the woven sleeve may be glued, tied, welded, or otherwise affixed to the catheter. The woven threads intersect in a weaving pattern and form crossover points at the intersections—knots may be located at the crossover points.

The invention also comprises a resector balloon system including an inner balloon and a woven sleeve. The woven sleeve includes at least one woven thread and crossover points where the woven thread intersects in a weaving pattern. The woven sleeve is disposed on a portion of the inner balloon. An outer balloon includes openings and an outer wall. The inner balloon and woven sleeve are disposed in the outer balloon. The outer balloon forms a space between the inner balloon and the outer balloon. The outer wall has a resecting surface for resecting biological material. Knots are located at the crossover points and at least partially extend through the openings in the outer balloon.

The inner balloon may be mounted to a catheter with at least one of its proximal and distal ends turned inward while the outer balloon is mounted to the catheter with at least one of its proximal and distal ends turned outward. The catheter may include a catheter lumen in fluid communication with the space between the inner and outer balloons. The balloon system may include a fluid source in fluid communication with the catheter lumen that provides fluid to the space between the inner and outer balloons. The balloon system may include a control system that controls the fluid source and the distance that the knots extend through the openings in the outer balloon by controlling the amount of fluid the fluid source provides the space between the inner and outer balloons. The woven sleeve may be weft knit. The woven thread may be elastic string or polyurethane string. The woven thread may include metallic or steel fibers. The woven sleeve may include at least one electrically conductive thread. The electrically conductive threads may include an electrically conductive core and an electrically insulative sheath or an electrically insulative core and an electrically conductive sheath. A proximal and distal portion of the woven sleeve may include electrically conductive threads while a middle portion of the woven sleeve may include electrically insulative threads. The balloon may be coupled to a catheter, and a proximal and distal end of the woven sleeve may be coupled to the catheter. The proximal and distal ends of the woven sleeve may be glued to the catheter.

The invention also includes a resector balloon system including a catheter coupled to a resector balloon and an outer wall of the resector balloon. The outer wall has a resecting surface for resecting biological material. A fluid source inflates the resector balloon by supplying fluid to the resector balloon through the catheter. A woven sleeve includes at least one electrically conductive thread and is disposed on at least a portion of the outer wall. The woven sleeve forms at least a portion of the resecting surface. The resector balloon system also includes a fluid control system that controls the fluid source.

The woven sleeve may be electrically connected to an energy source and may deliver energy to a target tissue. The balloon may include at least one wire molded into the catheter for conducting energy from the energy source to the woven sleeve. A proximal and distal portion of the woven sleeve may include electrically conductive threads while a middle portion of the woven sleeve may include electrically insulative threads. A data collection system may be electrically connected to the woven sleeve and may measure the electrical impedance of the woven sleeve. The data collection system may deliver electrical impedance data to a central control system which calculates the distension of the woven sleeve based on the impedance data, calculates the diameter of the balloon based on the distension data, and sends instructions to the fluid control system which controls the fluid source based on the calculated diameter of the balloon. The central control system may deliver the diameter data to a user interface. The data collection system may measure the electrical impedance of materials in contact with the woven sleeve. The data collection system may deliver impedance data to the central control system which determines the tissue in contact with the woven sleeve. The central control system may determine the tissue in contact with the woven sleeve by comparing the impedance data to a lookup table. The fluid control system may control the fluid source based on the tissue in contact with the woven sleeve. The data collection system may deliver impedance data to the user interface. The central control system may deliver tissue identity data to the user interface. A proximal and distal portion of the woven sleeve may include electrically conductive threads while a middle portion of the woven sleeve may include electrically insulative threads. The balloon may include at least one wire molded into the catheter for electrically connecting the woven sleeve to the data collection system.

DETAILED DESCRIPTION

Figure 1:
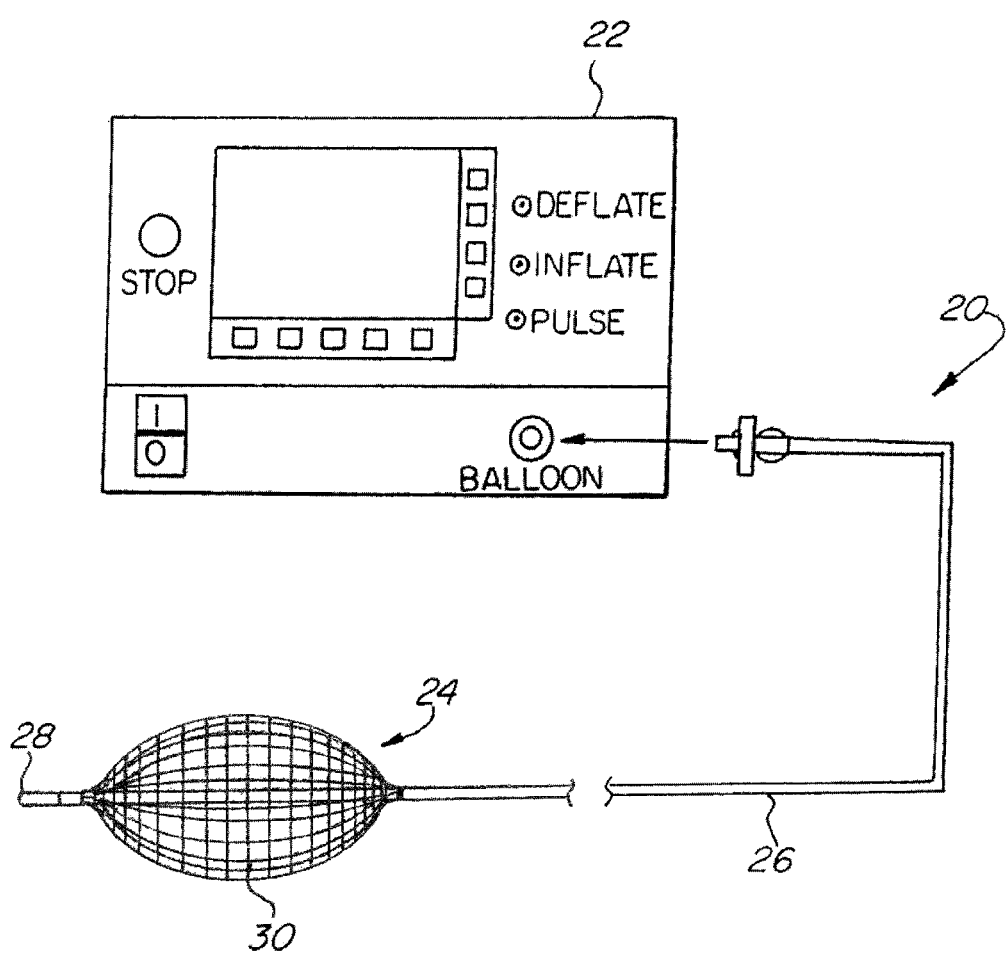
FIG. 1 is a partially schematic view of the resector balloon catheter system in accordance with the invention.

The basic components of one embodiment of a resector balloon system in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

The system 20, as shown in FIG. 1, includes a control system comprising a fluid source 22, such as an electropneumatic pump having controls on the front thereof, from which a physician or assistant can control the system (as well as a remote control unit), such as disclosed in U.S. Patent Application No. 2010/0121270 by Gunday et al., the specification of which has been incorporated by reference herein in its entirety. Fluid source 22 may also have a user interface having controls from which a physician or assistant can control the system 20, as further described below. A balloon catheter 24 is connected to control system, and fluid source 22 supplies a fluid, such as a gas, liquid, or mixture thereof, to balloon catheter 24. In certain cases, a cryogenic fluid is supplied by fluid source 22 in order to further aid a particular procedure, such as tumor desiccation.

The balloon catheter 24 includes a catheter 26 made of a polyethylene material and having an outer diameter of 1.8 mm and a length of about 1 to 2 meters. A bendable section 28 having a length of about 5 to 10 mm at the distal end of the balloon catheter 24 serves as a safety tip. As a result, when the catheter 24 is inserted through the available opening of a bodily cavity, it will bend instead of puncturing the walls of the cavity.

A balloon portion 30 made of latex, Yulex, or other suitable material is located near the distal end of catheter 26 or at an otherwise desirable, predefined distance along catheter 26. Balloon 30 comes in a variety of sizes and diameters, which can be selected to suit the particular application for which the device is being used. Typically, such balloons will have lengths of 5, 10, 15, 20, 30 or 50 mm and diameters of 2.5, 5, 10, 15, 20, 30 or 50 mm. This variety of available balloon sizes allows balloon catheter 24 to be used in bodily cavities of various diameters and dimensions, such as large and small bronchial branches, sinuses, and vessels, having different types of tumors and tissues to be treated. Fluid source 22 supplies the air at a pressure of approximately 2 atmospheres in order to be able to inflate such balloons to full size, ranging from 2.5 mml to 50 mml.

Each type of balloon that can be used with control system is characterized, and balloon profile data is registered in lookup tables. By identifying the type of balloon that is connected, the appropriate profile data can be retrieved and used to ensure that the appropriate pressure, volume, flow, and timing adjustments can be made to safely and effectively operate balloon 30. Alternatively, the balloon data can be included in a memory device such as an RFID device on the connector for the proximal end of the catheter. The balloon profile data contained in the lookup table, along with appropriate pressure and flow measurements (as further discussed below), allows one to make tissue density approximations. The inflation diameter/volume of balloon 30 can also be directly measured by measuring the changes in the electrical impedance and/or properties of a woven sleeve 34, as is further discussed below. This balloon profile data and approximated lumen diameter and tissue density, as well as any user commands, are used to adjust the amount of gas that fluid source 22 transmits to balloon 30 in order to achieve the desired inflation and deflation amounts. As is also further described below, the composition of a target tissue 1200 can also be more directly calculated by measuring its electrical impedance and/or properties using a woven sleeve 34 electrical circuit.

Figure 2:
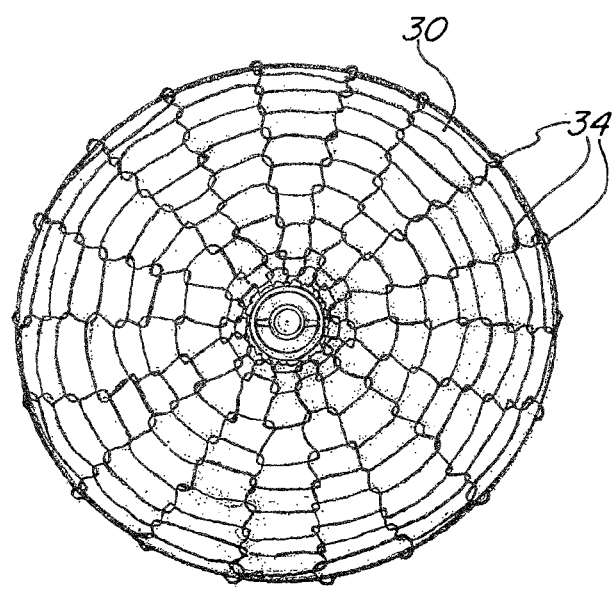
FIG. 2 is an end view of the inflated balloon of the system of FIG. 1.

Referring to FIG. 2, which shows a cross-section of the balloon 30, the balloon is covered with a woven sleeve 34 disposed on the surface of the balloon 30. Woven sleeve 34 can be made of threads comprising lycra, polyurethane, composite springs, metallic fibers, elastic, steel fibers, or other appropriate material, or a composite or coating thereof. Woven sleeve 34 can comprise electrically conductive threads. In some embodiments, the electrically conductive threads have an electrically conductive core and electrically insulative sheath. In other embodiments, the electrically conductive threads have electrically conductive sheaths or coatings and have electrically insulative cores. For example, the threads may be painted with an electrically conductive paint.

Figure 3:
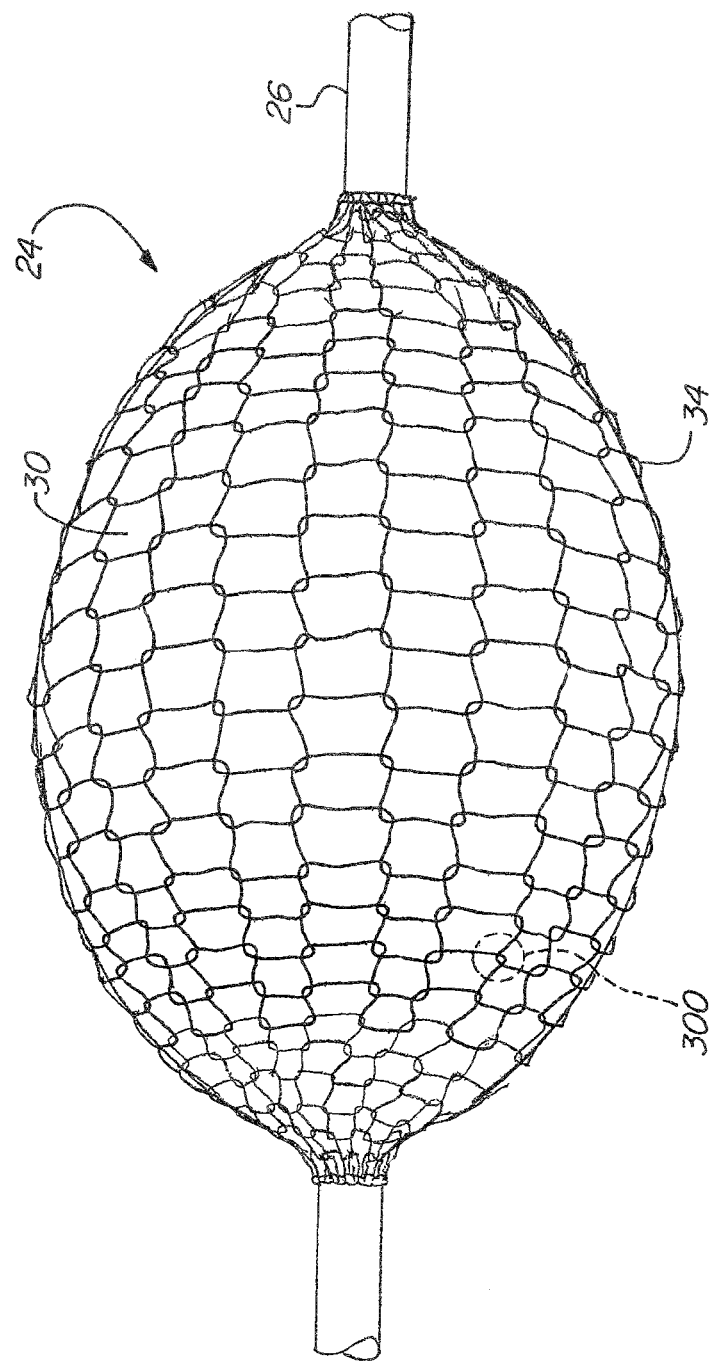
FIG. 3 is a side perspective view of the balloon of FIG. 2.

As shown in FIG. 3, woven sleeve 34 is at least partially disposed on resector balloon 30. This can be achieved by using a jig to expand the compressed tubular sleeve 34 and slide the woven sleeve over resector balloon 30. Alternatively, woven sleeve 34 may be knitted or woven from thread directly onto the resector balloon 30. Resector balloon 30 is then inflated, which expands woven sleeve 34, forming an expanded net structure and holding woven sleeve 34 in place. Crossover points 300 are points in woven sleeve 34 where the threads intersect in a weaving pattern. The proximal and distal ends of woven sleeve 34 are then coupled, glued, or welded to catheter 26, or tied down with suture-like material or held in place with shrink tubing, or an epoxied combination thereof. The jig may also be used to turn the tubular sleeve inside out before applying it to the balloon.

In operation, the resector balloon is inflated and deflated in the proximity of a target tissue. Woven sleeve 34 covers at least a portion of resector balloon 30 in an expanded net structure and adds texture, friction, and surface area to the resecting surface of resector balloon 30. The crossover points 300 of the threads produce outwardly-facing, small knots or dimples, which create micro-impacts on the tumor tissue (or other biological material to be resected) during the inflation/deflation cycles further described below. Thus, woven sleeve 34 will dislodge and collect and hold more tissue than the bare outer surface of resector balloon 30 would. After a procedure, woven sleeve 34 can be cut or otherwise removed from catheter 26 and resector balloon 30. The used woven sleeve 34 can then be submitted to a lab for tissue analysis and/or biopsy of the collected target tissue which has adhered to woven sleeve 34 during the operation.

Figure 4:
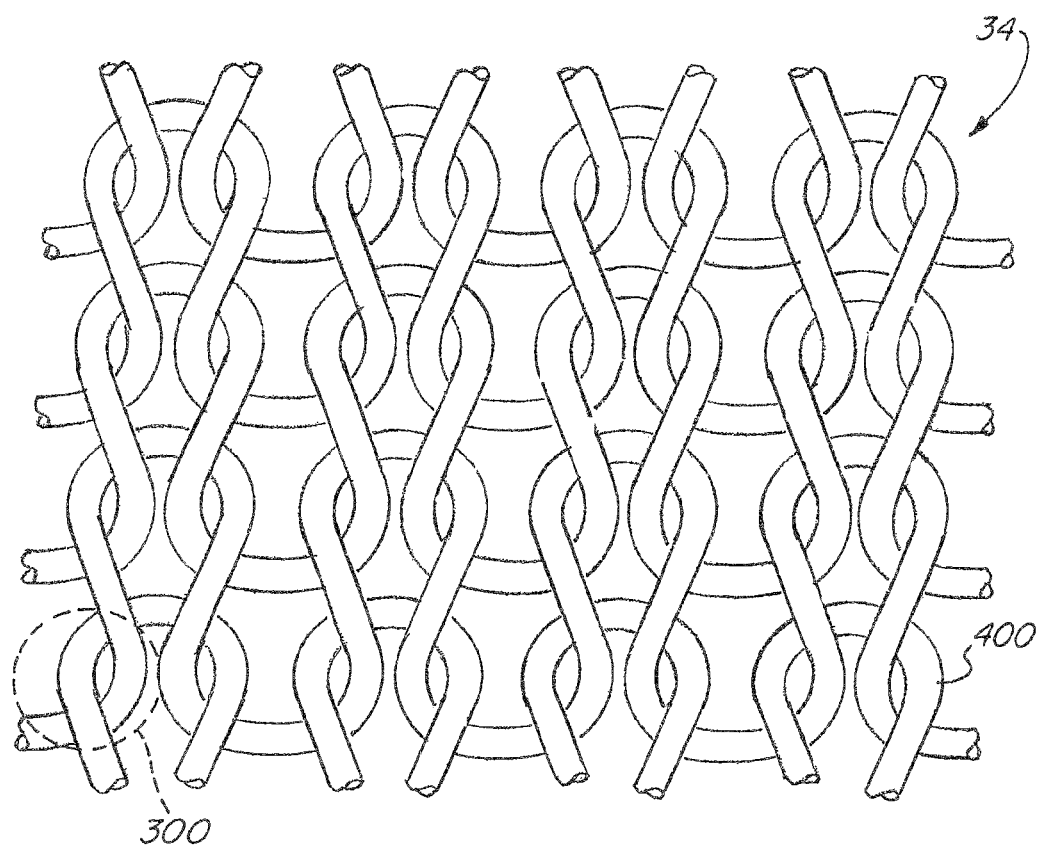
FIG. 4 is a side perspective view of a portion of the woven sleeve disposed on the balloon of FIG. 2.

FIG. 4 shows a blown-up example of a weft knit pattern on a portion of a tubular woven sleeve 34 in two dimensions. Threads 400 are woven in the pattern shown. The threads 400 intersect at crossover points 300 in the weft knit pattern. In FIG. 4, woven sleeve 34 and the knitting of the fabric therein are in a compressed tubular condition; whereas, in FIG. 3, woven sleeve 34 and knitting have been expanded into an expanded net structure.

During the knitting process, the size of the knitting thread, the number of needles, the spacing between the needles, the tension on the yarn from the spool, the tension on the tubular knitted sleeve, the type of spooling of the supply yarn, among other parameters, are controlled to achieve a tubular mesh sleeve with the desired outer diameter and tension.

Figure 5:
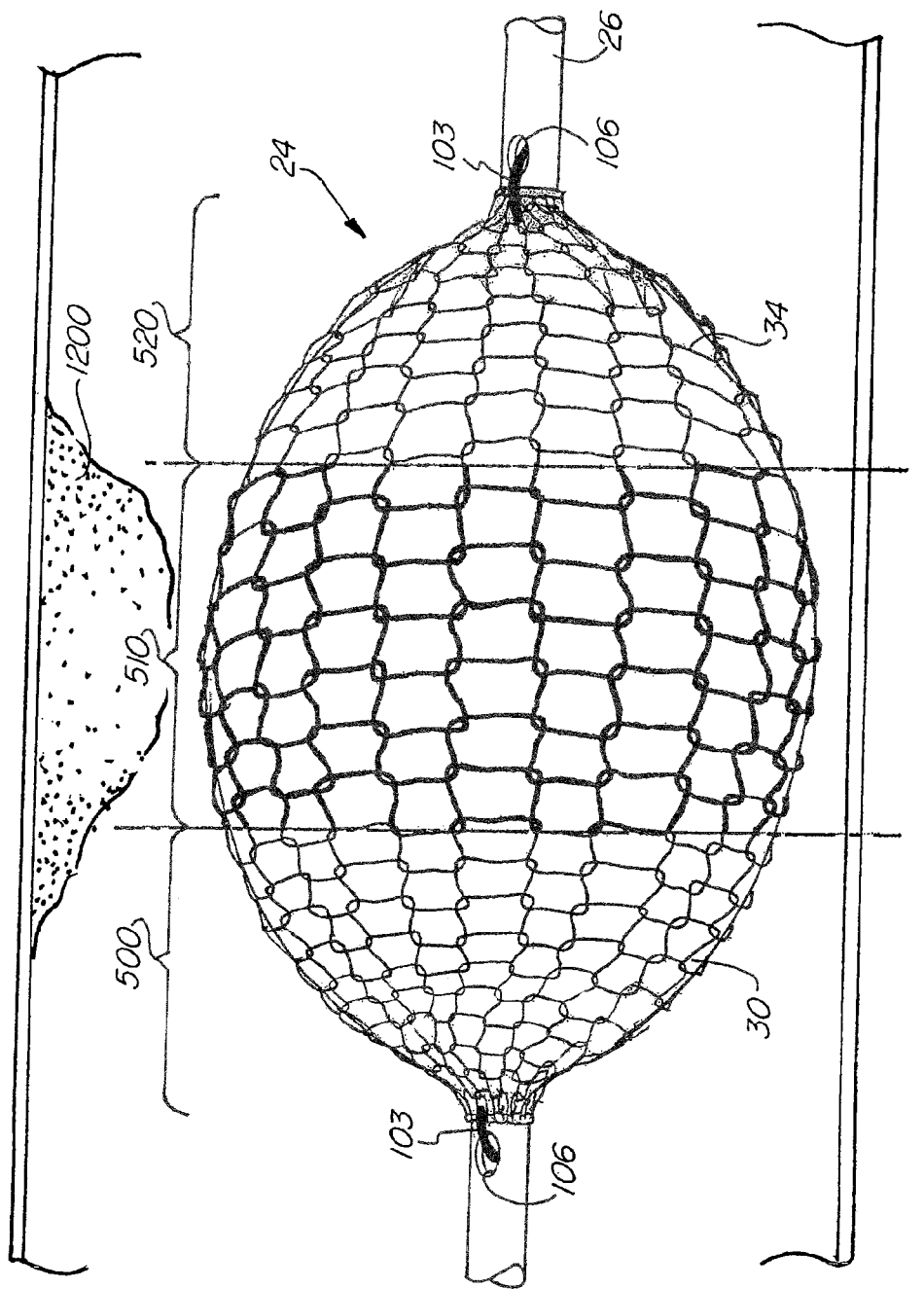
FIG. 5 is a side perspective view of the balloon of FIG. 2 with electrically conductive and insulative sections.

Referring to FIG. 5, in certain advantageous embodiments, woven sleeve 34 comprises a proximal portion 500, a middle portion 510, and a distal portion 520, where proximal portion 500 and distal portion 520 comprise electrically conductive threads 400, while middle portion 510 comprises electrically insulative threads 400. Electrical wires 103 run through catheter 26 and protrude from access holes 106, and are electrically coupled to proximal portion 500 and distal portion 520. Because the target issue 1200 is electrically conductive, with various impedances depending on the type of tissue, an electrical circuit can be completed by the target tissue 1200 between proximal portion 500 and distal portion 520.

Electrically conductive yarn has the characteristic of changing its impedance (i.e., resistance) as it is expanded, for example, when the balloon is inflated. Such yarn can also have the characteristic of being radio opaque. This is achieved by adding metal fibers to the yarn during production or by coating the yarn. Additionally, yarn with metal fibers can be combined with plain yarn selectively produced or introduced during the knitting process.

First, this configuration improves energy delivery to target tissue 1200 during a procedure.

Additionally, this configuration also allows for improved measurement of the characteristics of target tissue 1200, as one can measure the electrical impedance of target tissue 1200 in this way. These improvements are a result of the fact that tissue 1200 is placed in series with the energy delivery or measurement circuit in this configuration. Thus, the tissue behaves in a circuit element and is more directly measured or affected by the circuit. The tissue can then be identified in various ways. For example, one could also take measurements of multiple areas, including target tissue 1200 and nearby healthy tissue (i.e., the wall of the bodily cavity below section 510 of the woven sleeve 34 in FIG. 5) and compare these measurements to determine when a target area does or does not contain undesirable biological material. Alternatively, one can compare a measurement of the tissue 1200 to known impedances for tissue types in a lookup table, as described below.

In other embodiments, the entire woven sleeve 34, including proximal portion 500, middle portion 510, and distal portion 520, are woven with electrically conductive thread 400. This configuration permits energy delivery to target tissue 1200 and measurement of electrical properties of target tissue 1200.

This also permits precise measurement of the diameter or state of inflation of balloon 30. The impedance in the woven sleeve 34 may be measured because it is woven to precisely set the tension of woven sleeve 34. As woven sleeve 34 is expanded, its electrical impedance changes. This impedance change can be measured via wires 103 as further discussed below. This data can be used to determine the state of inflation of balloon 30 (and the tissue 1200 surrounding the catheter) and to regulate this inflation.

Additionally, crossover points 300 may electrically isolate two intersecting threads. Thus, energy delivery may be selectively triggered for different portions of tissue 1200 simultaneously. Furthermore, different portions of tissue 1200 may be analyzed electrically. In this way, multiple electrical circuits can be fashioned on the surface of the balloon.

Figure 6:
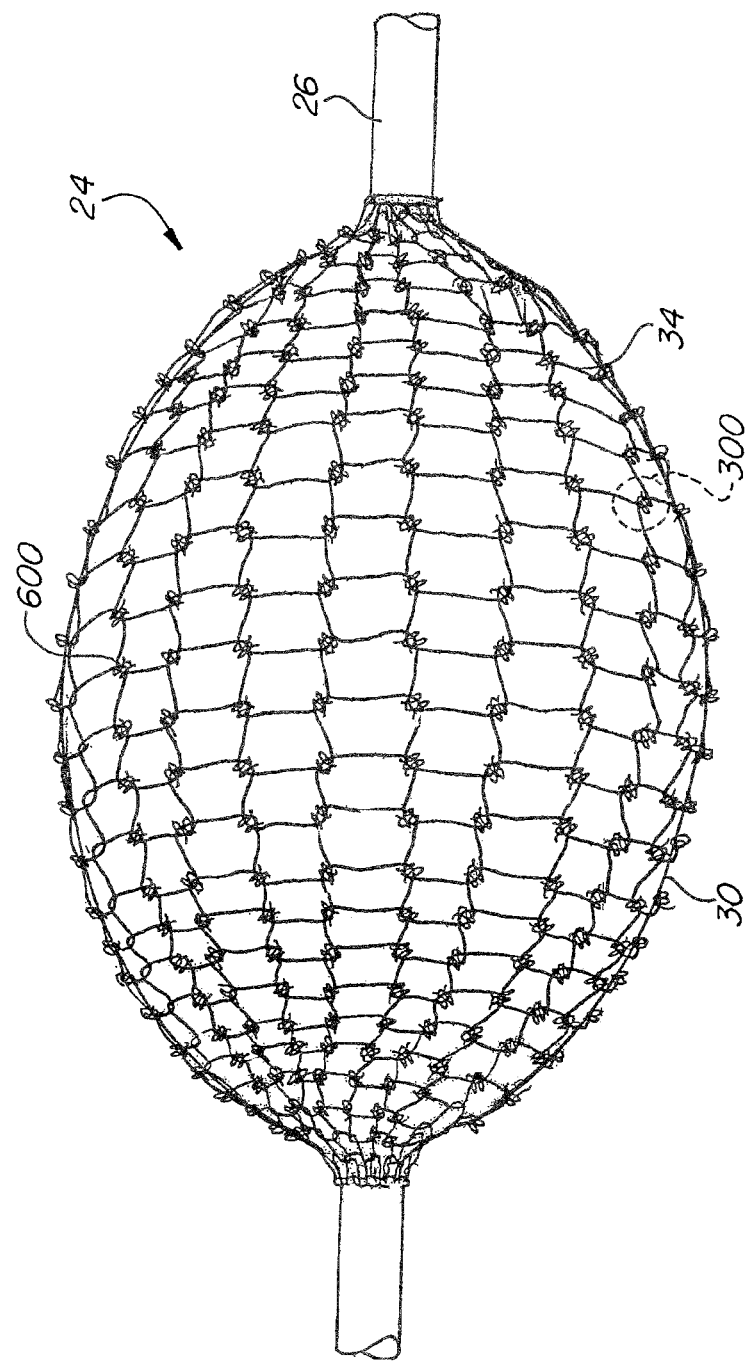
FIG. 6 is a side perspective view of the balloon of FIG. 2 with knots at the crossover points.

Referring to FIG. 6, in some embodiments, woven sleeve 34 comprises knots 600 at the crossover points 300. In one embodiment, knots 600 are formed as part of the weaving process. Knots 600 add additional texture, friction, and surface area to woven sleeve 34. Knots 600 may be double knots to increase the length or surface area thereof. Knots 600 also enhance energy delivery to tissue 1200 by enhancing surface area and penetration of the contact points between woven sleeve 34 and tissue 1200. Thus, woven sleeve 34 will typically dislodge and collect more tissue 1200 than a woven sleeve 34 without knots 600. It will also typically deliver more energy and better measure tissue electrical properties than a woven sleeve 34 without knots 600.

Figure 7:
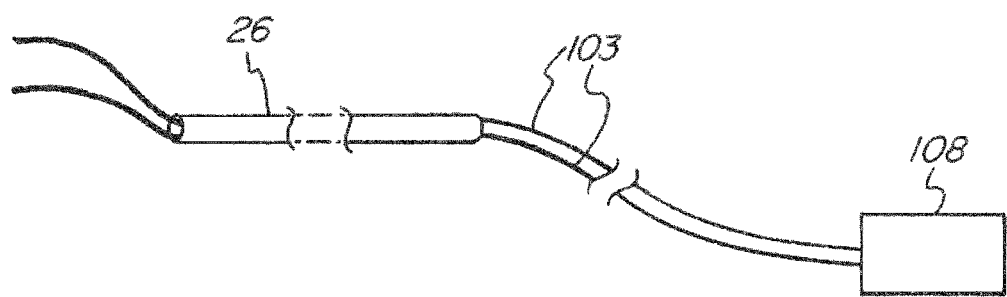
FIG. 7 is a partially schematic view of a catheter of the system of FIG. 1.

As illustrated in FIG. 7, in certain embodiments, catheter 26 with electrically conductive wires 103 is used to deliver energy to a desired biological material 1200 to be treated. The electrically conductive wires 103 are molded into the catheter 24 and electrically insulated from one another. The distal ends of the wires 103 are, in turn, connected to an energy generating device 108 for supplying the requisite energy such as, for example, a suitable electro-surgical unit. As previously shown in FIG. 5, the proximal end of electrically conductive wires 103 are routed through access holes 106 and electrically coupled to woven sleeve 34. In these cases, safety precautions must be taken to prevent overheating and popping of the balloon.

It should be noted that both monopolar (single conductor energy source) and bipolar (dual conductor energy source) implementations may be employed. The single source may be connected to wires 103 connected at opposite ends of woven sleeve 34, or a single wire or wires connected at one end of woven sleeve 34. Similarly, bipolar sources may be electrically connected to one or both ends of woven sleeve 34. In this way, various forms and types of energy, such as radio-frequency and electrosurgical energy, can be supplied in a 360° fashion to perform ablation, cauterization, excision, decortications, and/or tissue modification in order to optimize hemostasis and resection. A similar energy delivery system can be constructed for delivery of ultrasound. In this way, the various forms of energy may be delivered through woven sleeve 34 to the target tissue 1200.

In certain advantageous embodiments, system 20 includes insulating materials and insulation barriers along and within the surfaces of the balloon construct to insulate balloon 30 from the thermal, ultrasonic, and associated deleterious effects of the different forms energy delivered by the above described system. Accordingly, balloon 30 is protected against becoming deflated or otherwise comprised under the stress of the energy delivery process(es).

Figure 8:
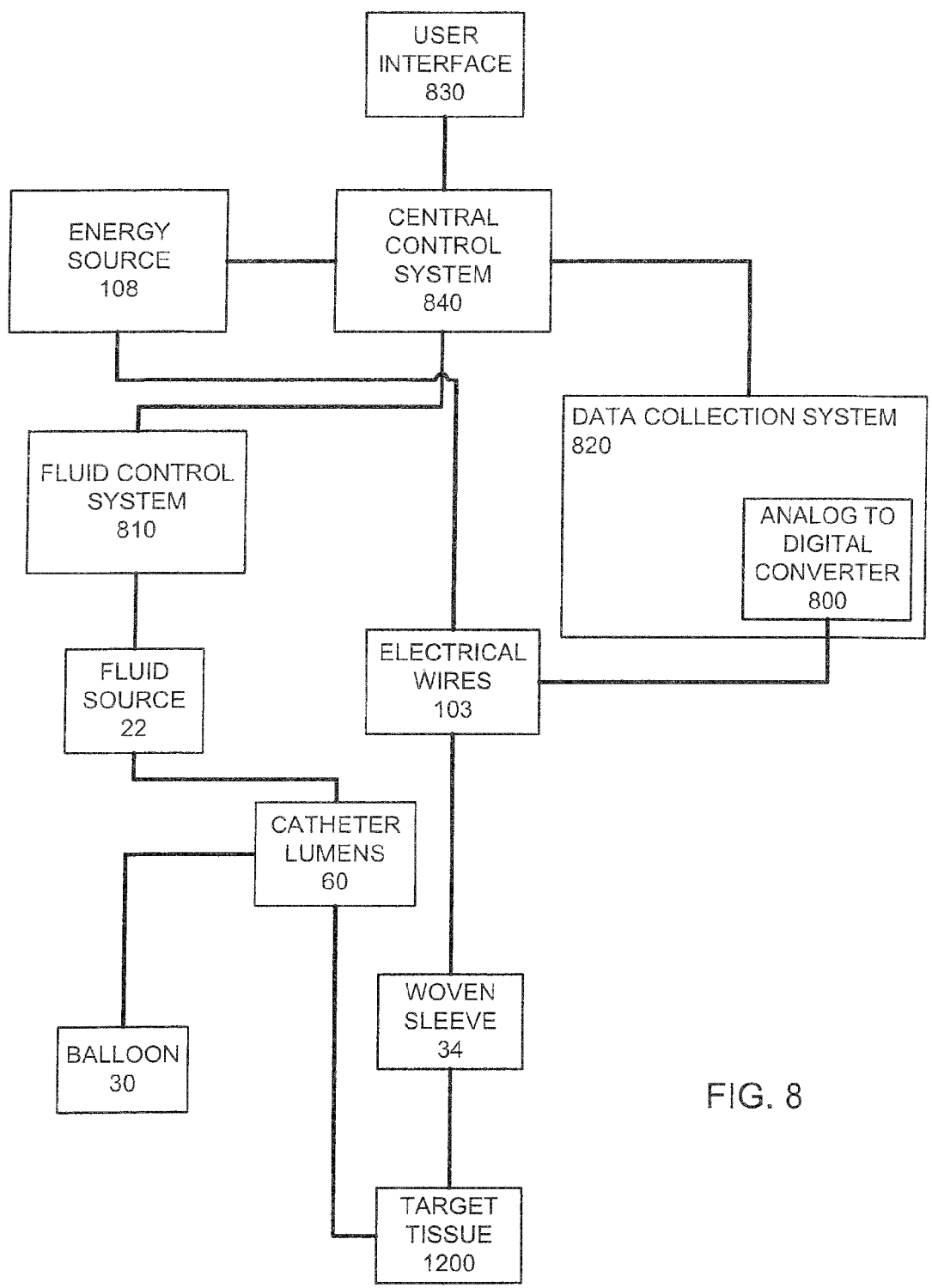
FIG. 8 is a block diagram of another embodiment of the catheter system of FIG. 1.

FIG. 8 shows a block diagram of the balloon catheter system 20. Central control system 840 is connected to a data collection system 820 and a fluid control system 810. Data collection system 820 comprises Analog-to-digital converter (ADC) 800. ADC 800 is electrically coupled to woven sleeve 34 via electrical wires 103. Energy source 108 is electrically coupled to woven sleeve 34 via electrical wires 103. Central control system 840 may be connected to energy source 108 to vary energy delivery to woven sleeve 34. Central control system 840 is also connected to user interface 830, which in some embodiments contains a display and input means. Central control system 840 is connected to fluid control system 810. Fluid control system 810 is connected to a fluid source 22, which is connected via catheter lumens 60 to balloon 30 or directly to target tissue 1200. Woven sleeve 34 is electrically and mechanically connected to target tissue 1200 as discussed above. In some embodiments, user interface 830, central control system 840, energy source 108, fluid source 22, data collection system 820, ADC 800, and fluid control system 810 are all contained within a single unit. The data collection system 820 includes input for parameters from the fluid source, such as pressure, volume, and flow.

A constant, known voltage (or voltage-varying signal) is applied across woven sleeve 34 by data collection system 820, energy source 108, or some other source. ADC 800 measures the change in current over time and converts and digitizes the signal so that the central control system 840 can analyze it. It should be appreciated that a known current (or current-varying signal) could be supplied across woven sleeve 34 and ADC 800 could measure voltage changes to perform the same function. In embodiments where the entire woven sleeve 34 is electrically conductive, ADC 800 can measure the diameter of the balloon because the impedance of woven sleeve 34 will reliably change as a function of its degree of distension. Thus, values collected by ADC 800 can be compared to a lookup table (LUT) in the central control system 840 or data collection system 820 as an added verification of the degree of balloon inflation. This information can be displayed to a user via user interface 830 via a display system within the user interface.

Some embodiments, such as that shown in FIG. 5, have a woven sleeve 34 having an electrically insulative center band (corresponding to the widest portion of balloon 30). In these embodiments, the same arrangement as described above could be employed. In this embodiment, it may be preferable to apply a known voltage or voltage signal, or signals at varying frequencies, as there will be no baseline current. In this embodiment, the surrounding tissue 1200 and fluid bridges the circuit gap in the central band of woven sleeve 34. Different tissues have different known impedances. Thus, a LUT containing known tissue impedances could be compared by the central control system 840 to the data collected by ADC 800. This information is transmitted to an operating physician via user interface 830, as it is advantageous for a medical professional to know what tissue is being contacted/resected by balloon 30. For example, a physician may be resecting a tumor and notice a sudden change in the measured impedance, indicating that balloon 30 has come in contact with healthy tissue. This would be an additional indicator to the physician that he should stop resecting tissue to prevent unwanted injury to the patient. The physician can then instruct central control system 840 to cease inflation of the balloon 30 via user interface 830.

Figure 9:
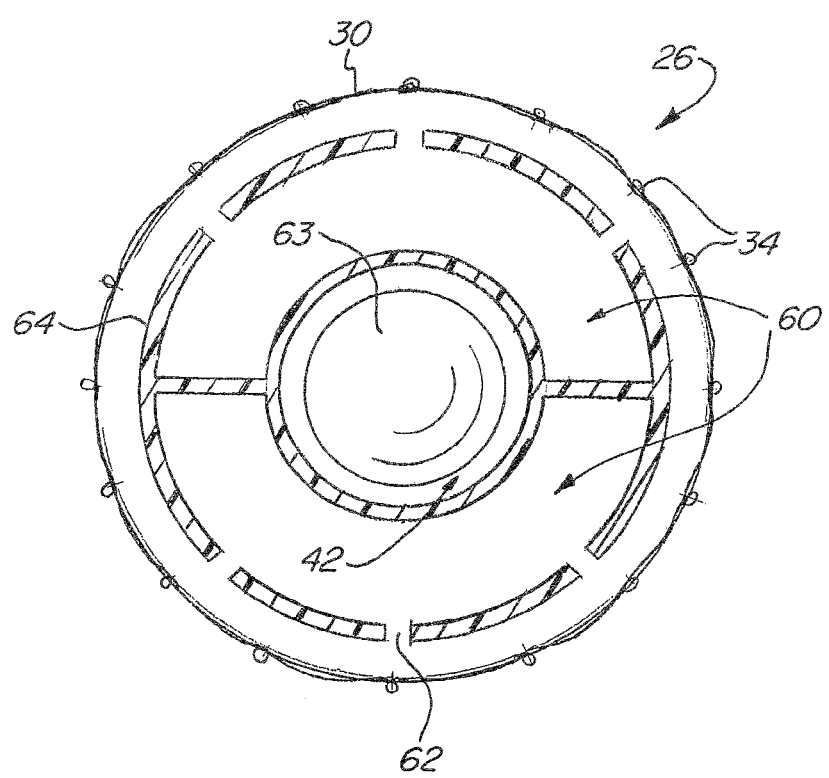
FIG. 9 is a cross-sectional, end view of the catheter of the system of FIG. 1.

FIG. 9 shows a cross-section of a catheter 26 for use with several embodiments of resector balloon 30. Outer lumens 60 of catheter 26 are used to inflate and deflate balloon 30 through holes 62 provided in the catheter's outer wall 64. These outer lumens 60 are blocked at the distal end of balloon 30 so that air or fluid intended for inflation and deflation will not escape. Inner lumen 42 can be used as an air bypass, to communicate fluid, or to delivery drugs or other agents. In some embodiments, a guide wire 63 is disposed in inner lumen 42 to furnish catheter 26 with desirable mechanical properties such as strength, axial rigidity, and lateral flexibility.

Outer lumens 60 can also be used to deliver diagnostic or therapeutic agents, such as, for example, a medicinal drug via holes in catheter 26 located proximally or distally of the balloon 30. In this way, the drug is delivered to a targeted site and evenly distributed. It should be noted that, however, in other embodiments, such drugs or other agents may be dispersed through multiple distal tips or through orifices in the lateral walls of the balloon. Accordingly, such agents can be released via a methodic and/or timed release.

Lumens 60 and holes 62 can be used to deliver any number of things to assist with opening the cavity, circulation, aspiration, respiration, assisting the decomposition of an obstruction, or stimulating healing in the affected area, including air, aspirates, drugs, biologics, biogenetic agents, nano-particulates, solutions, stem cell and gene therapies, and stents and scaffolds. Specifically, the device could be used for the deployment and implantation of pro-generative vehicles and/or catalysts in the repair, treatment, and therapy of the targeted areas, including biologic, nano-particulate materials and/or biogenetic materials, structures, scaffolds, and similar devices and vehicles, including, for example, bone morphogenetic proteins, microcrystalline nano-particulates, collagens, de-mineralized bone chips, calcium based structures, poly glycolic acids, poly lactic acids, and hyaluronic acids. The device can likewise be used for the deployment and implantation of inert, inelastic, and semi-rigid materials, such as, for example, PEEK, ceramic, cobalt chrome, titanium, and stainless steel, and for the implantation of reinforcing constructs within, along, and/or around anatomic structures, which may be deployed and then impregnated, impacted, and otherwise filled, either prior to or after insertion, with inert materials including, for example, polymethyl meth-acrylate, bone cements, polyethylene, polypropylene, latex, and PEEK.

Figure 10:
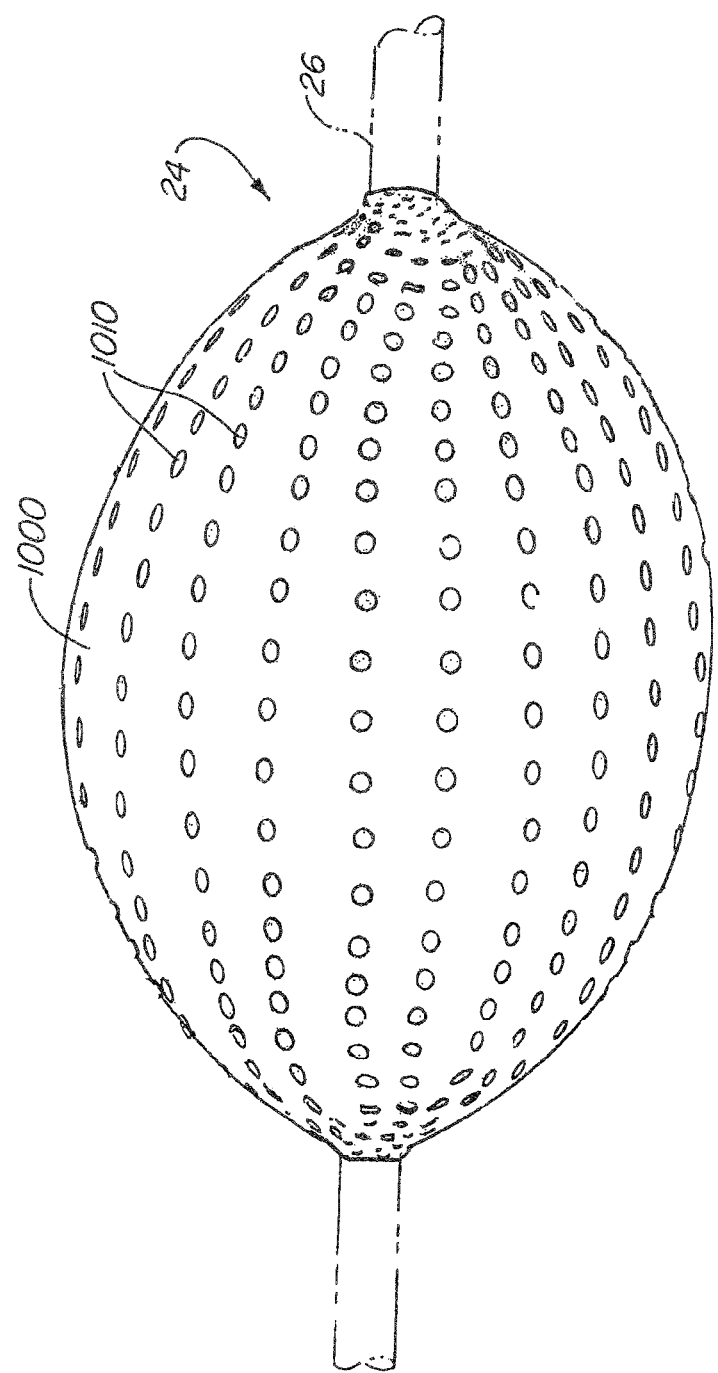
FIG. 10 is a side, perspective view of the balloon of FIG. 6 with a perforated outer balloon disposed thereon.
Figure 11:
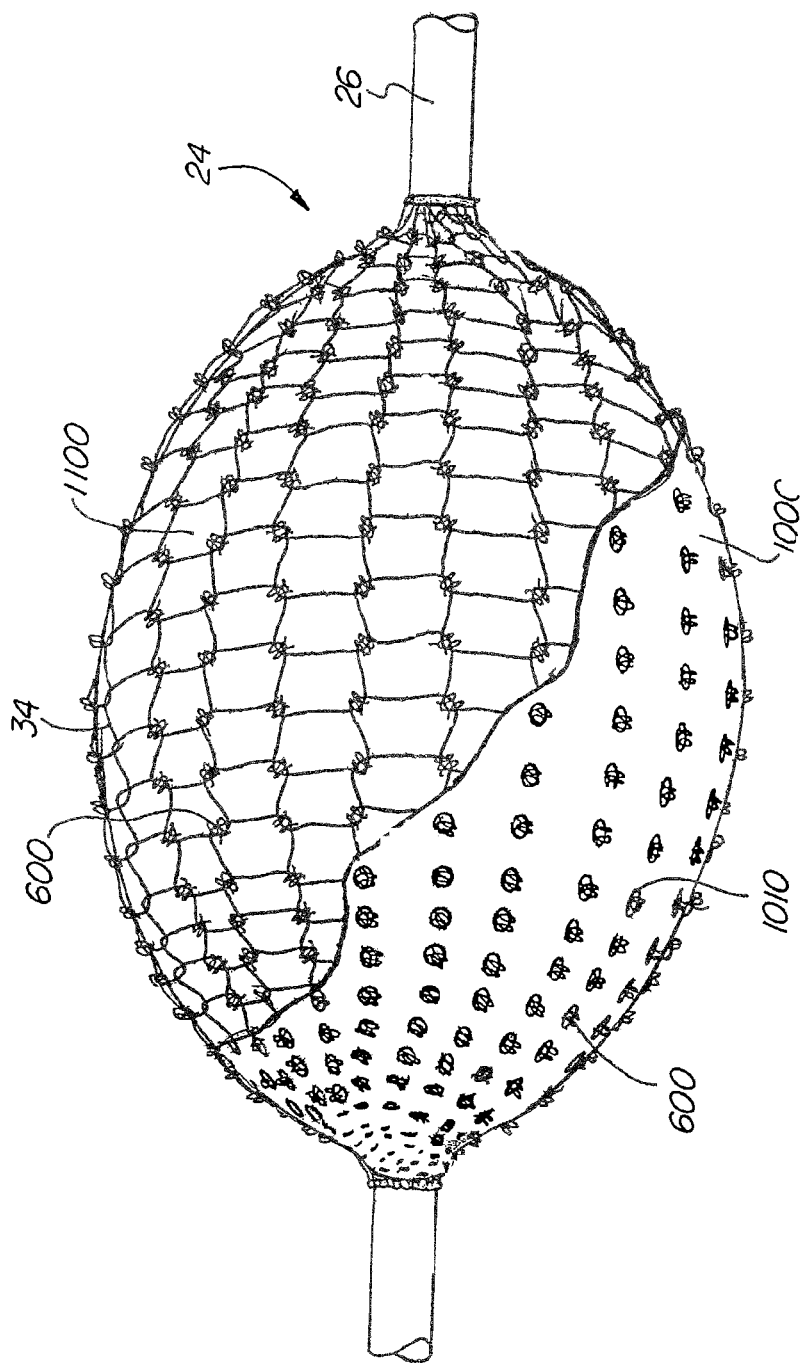
FIG. 11 is a partially exposed side perspective view of the balloon of FIG. 10.

FIGS. 10 and 11 feature side views and a cutaway of an embodiment of balloon catheter 24. Balloon catheter 24 comprises an inner balloon 1100 and an outer balloon 1000. Outer balloon 1000 comprises an outer wall having openings 1010 thereon. Balloon catheter 24 comprises woven sleeve 34 which is at least partially disposed on inner balloon 1100. As previously noted, woven sleeve 34 comprises knots 600 at crossover points 300. Inner balloon 1100 and woven sleeve 34 are disposed in outer balloon 1000, producing a space between inner balloon 1100 and outer balloon 1000. Knots 600 are aligned with openings 1010 and at least partially extend through openings 1010. The catheter lumen 60 is in fluid communication with the space between inner balloon 1100 and outer balloon 1000 via at least one opening 62. This layering also allows for the use of multiple sleeves isolated from one another.

In operation, a fluid source 22 and/or control system 100 can regulate the distance that knots 600 penetrate openings 1010 and/or extend from an outer surface of outer balloon 1000. Regulating this distance is accomplished by controlling the fluid flow to the space between outer balloon 1000 and inner balloon 1100, thus regulating its level of inflation. The level of inflation correlates with the amount of separation between outer balloon 1000 and inner balloon 1100 and the size of the space therebetween. The more inflated the space is, the less the distance that knots 600 will extend through openings 1010. In other embodiments, the degree of inflation between outer balloon 1000 and inner balloon 1100 is maintained at a constant level, the degree of inflation of the inner balloon 1100 is adjusted in order to adjust the distance that knots 600 will extend through openings 1010.

In some embodiments, the space between outer balloon 1000 and inner balloon 1100 is inflated with a liquid, such as a drug solution or suspension. In such embodiments, holes 62 would need to be arranged at a specific location on catheter 26 which is in fluid communication with the space. In most embodiments and conditions, fluid will leak through openings 1010 and be introduced to the resecting environment and target tissue 1200. The fluid source and/or control system must maintain a pressure differential between the space and surrounding environment to keep the space inflated. This is possible with sufficient inflation despite the leakage through openings 1010. This leakage is an advantageous way to deliver drugs to the resecting environment and the surrounding tissue 1200.

The texture, friction, and surface area of the resecting surface can therefore be adjusted in real time using this balloon catheter 24, because the distance that knots 600 extend from outer balloon 1000 varies the surface area. The energy delivery efficiency or electrical coupling efficiency between woven sleeve 34 and tissue 1200 can also be varied because these properties also depend on the level of knot 600 protrusion. An operator can make adjustments mid-procedure to increase or decrease the rate of resection or energy delivery. An operator can also make adjustments as the target tissue 1200 consistency changes as it is being resected. An operator may desire to resect at multiple locations during a single procedure, and adjusting the texture of the resecting surface or properties energy delivery may be advantageous.

Figure 12A:
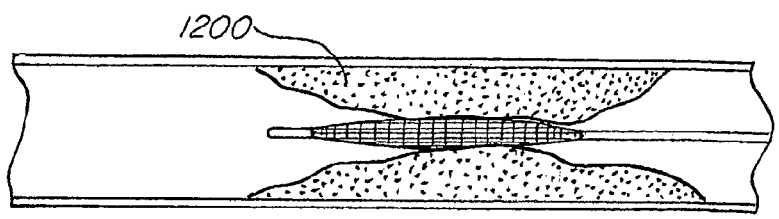
FIGS. 12A-12F are side perspective views of the balloon of FIG. 2 being used to remove and collect tissue from a body cavity.

FIGS. 12A-12F are illustrations of an embodiment of resector balloon 30 being used to remove and collect tissue 1200. As shown in FIG. 12A, the balloon 30 is first inserted and positioned adjacent a target tissue in a deflated state.

Figure 12B:
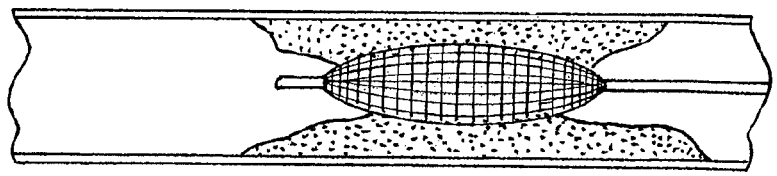

Referring next to FIG. 12B, the balloon is then inflated by fluid source 22 (which knows the type of balloon to which it is connected) at an air pressure of approximately 2 atmospheres for a fixed amount of time, and the flow is measured (after the physician presses an inflate button on the fluid source). This data combined with other data collected from woven sleeve 34 is used to calculate the initial approximation of the density of target tissue 1200 and the size of the opening in the tumor tissue 1200, and displays the results for confirmation by the physician. As fluid source 22 is operated, this data is continuously updated and displayed.

Figure 12C:
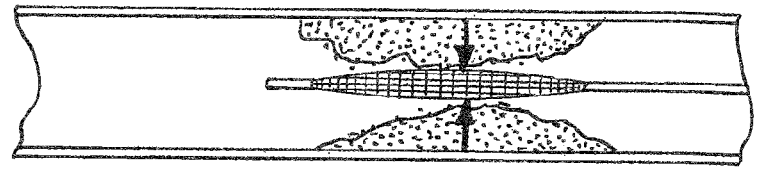
Figure 12D:
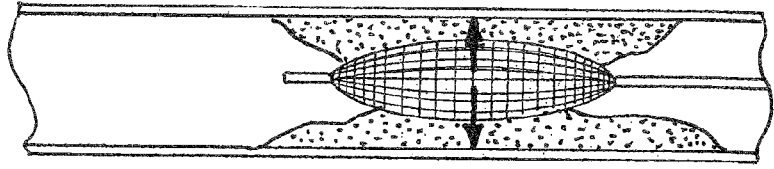

As shown in FIGS. 12C-D, fluid source 22 is then put in pulse mode and balloon 30 is deflated and inflated in a cyclical fashion, based either on parameters that were entered by the user, or on default parameters selected by fluid control system 810, which are based on the characteristics of the particular balloon (which has been identified as a result of a balloon identification plate affixed to balloon 30 or balloon catheter 24) and the diameter and/or density measurements made by the system. In this way, the pulse mode of fluid control system 810 causes balloon 30 to pulsate according to a desired frequency or change in volume within balloon 30, producing a periodically recurring increase and decrease in the size of balloon 30. Even though balloon 30 could deflate faster with a vacuum source, the elasticity of the woven sleeve 34 and latex balloon 30 will still generate sufficient frequency to make it useful.

Accordingly, the resecting surface of balloon 30 repeatedly comes into contact with the tissue growth, tumor, or other unwanted obstruction to create micro-impacts thereon. As balloon 30 is deflated and inflated, the resecting surface creates just enough interference fixation, concentrically, along with compressive force excitation and friction upon the unwanted biological material 1200, to promote compressive force exhaustion and abrasion to elicit the decomposition and excision thereof, such that the targeted biological material is resected in a non-traumatic way. As tissue 1200 is destroyed and removed, balloon 30 is inflated to a larger starting diameter and these steps are repeated until all the unwanted tissue 1200 is resected.

Meanwhile, fluid control system 810 continually monitors the pressure of balloon 30 and fluid flow, sends the data to central control system 840 and/or user interface 830 and updates user interface 830 or a display system therein as is further described below. This gives the physician an indication as to when to stop the pulse mode and evacuate the loosed tissue 1200.

Figure 12E:
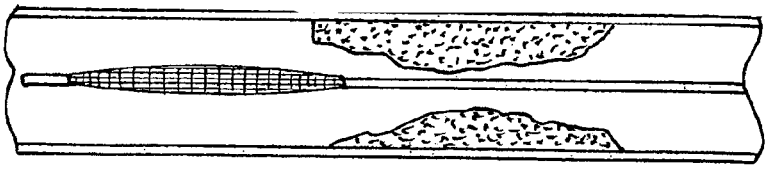

Referring to FIG. 12E, once the tumor and/or tissue 1200 is broken up, balloon 30 is deflated (by instructing fluid control system 810), and balloon 30 is inserted further distally into the bodily cavity, past the location of unwanted tissue 1200.

Figure 12F:
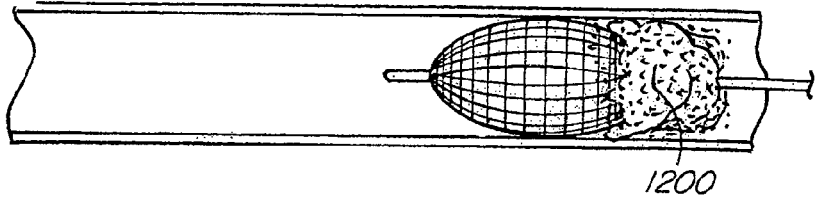

A shown in FIG. 12F, balloon 30 is then re-inflated (by instructing fluid control system 810) and gently pulled towards the proximal end, bringing with it loose tissue 1200 and debris to a point where it can be removed using forceps or suction. Some of tissue 1200 will adhere to woven sleeve 34, which can then be removed and submitted to a lab for analysis and/or biopsy. Alternatively, the debris can be suctioned out with conventional methods.

The data collected from pressure and flow readings combined with electrical data collected from woven sleeve 34 is used by a central control system 840 which in some embodiments contains a microcontroller that makes the appropriate pressure and timing adjustments necessary to maximize the effectiveness of balloon 30, provide the physiologic metrics of the affected and non-affected areas, and provide data points and indicators related to the specific dimensional and density characteristics of the intra-lumen anatomy and pathology to aid the physician in safely determining and delivering treatment.

Figure 13:
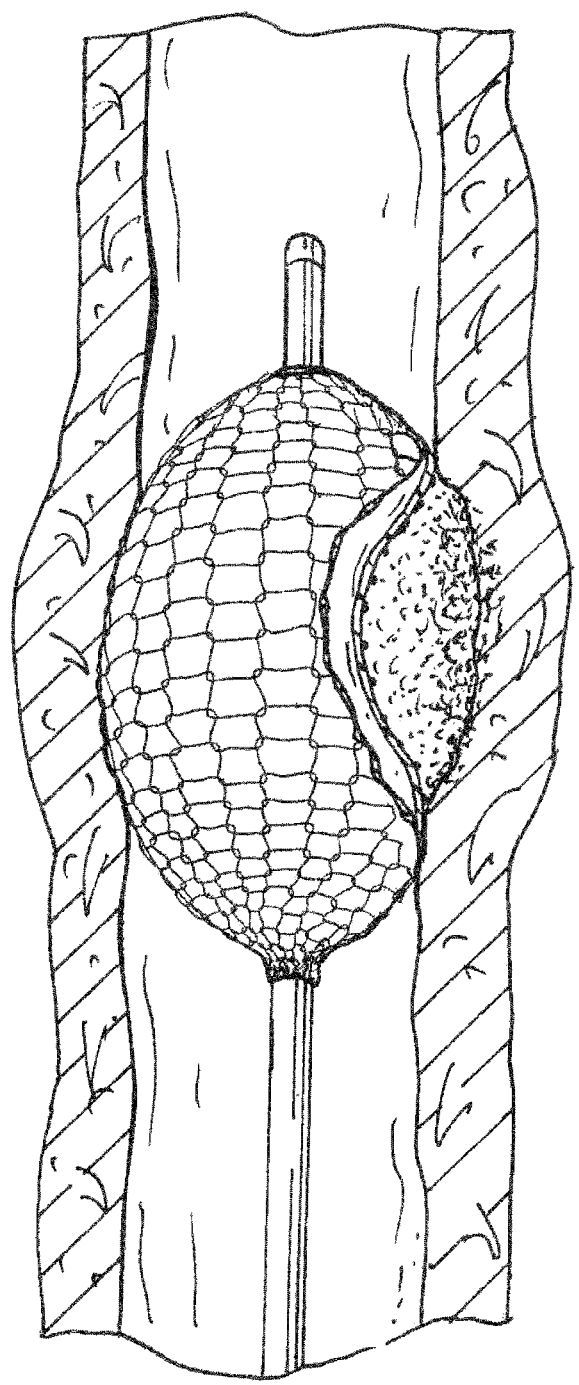
FIG. 13 is a side perspective view of the balloon of FIG. 2 conforming to the shape of a bodily vessel with a constriction therein.

FIG. 13 is a partially exposed view of the balloon 30 with woven sleeve 34 inserted in a constricted bodily vessel. As the balloon 30 conforms to the shape of the obstruction, the impedance in that portion of the sleeve 34 changes, allowing the shape and size of the obstructed vessel to be measured and a three-dimensional image thereof to be rendered on a display. Similarly, the sleeve 34 may be radio opaque, thereby allowing external, indirect imaging, such as with a mobile CT scanner, such that the balloon can be scanned and a three-dimensional rendering can be displayed on a screen.

The above-described system can also be used for minimally invasive interventional treatment for Facet Joint fusion. A unique dimensionally shaped balloon that mimics the articular surfaces of the facet joint is deployed to the facet joint via wire guidance under endoscopic and/or fluoroscopic visualization and then inflated. The abrasive mesh-like surface of balloon 30 is concentrically and radially pulsed to create micro-abrasions upon the articular cartilage, and ablative energy is then applied to the electrically conductive threads 400 in woven sleeve 34, eliciting decomposition and decortication of the articular surface. Any bleeding is tamponaded by inflating balloon 30 to create compression and/or via application of electrosurgical energy that is transmitted via the electrically conductive threads 400 in woven sleeve 34. Balloon 30 is then rotated to further decorticate and widen the articular space. Balloon 30 is then deflated, and an inert implant, bone dowel, or other osteo-conductive and osteo-promotive biologic implant is then inserted along the deflated catheter and/or guide wire and into the articular joint space to create an interference fit and promote fusion. An iteration of this procedure would also include the deployment of a facet joint replacement implant. This procedure has broad application across the broad spectrum of articular joint fusion and articular joint replacement. Detailed articular mapping can be achieved, measuring both convexities and concavities, thereby providing comprehensive real-time analysis on the geometries of the anatomy.

Although the invention has been described with reference to embodiments herein, those embodiments do not limit the scope of the invention. Modifications to those embodiments or different embodiments may fall within the scope of the invention.

What is claimed is:

1. A resector balloon, comprising:
   a resector balloon having an outer wall, wherein the outer wall comprises a resecting surface that resects biological material; and
   a woven sleeve comprising at least one woven thread disposed on at least a portion of the outer wall, wherein the woven sleeve forms at least a portion of the resecting surface;
   crossover points where the woven threads intersect in a weaving pattern; and
   knots located at the crossover points.

2. The resector balloon of claim 1, wherein the woven sleeve is weft knit.

3. The resector balloon of claim 1, wherein the at least one woven thread is elastic string.

4. The resector balloon of claim 1, wherein the at least one woven thread is polyurethane string.

5. The resector balloon of claim 1, wherein the at least one woven thread comprises metallic fibers.

6. The resector balloon of claim 5, wherein the at least one woven thread comprises steel fibers.

7. The resector balloon of claim 1, wherein the woven sleeve comprises at least one electrically conductive thread.

8. The resector balloon of claim 7, wherein the electrically conductive threads comprise an electrically conductive core and an electrically insulative sheath.

9. The resector balloon of claim 7, wherein the electrically conductive threads comprise an electrically insulative core and an electrically conductive sheath.

10. The resector balloon of claim 7, wherein a proximal portion and a distal portion of the woven sleeve comprise electrically conductive threads and a middle portion of the woven sleeve comprises electrically insulative threads.

11. The resector balloon system of claim 7, wherein the woven sleeve is electrically connected to an energy source that transmits electrical energy to a target tissue via the woven sleeve.

12. The resector balloon of claim 11, further comprising:
at least one wire molded into the catheter for conducting energy from the energy source to the woven sleeve.

13. The resector balloon of claim 11, wherein a proximal portion and a distal portion of the woven sleeve comprise electrically conductive threads and a middle portion of the woven sleeve comprises electrically insulative threads.

14. The resector balloon system of claim 7, further comprising:
a data collection system electrically connected to the woven sleeve.

15. The resector balloon system of claim 14, wherein the data collection system obtains the electrical impedance of the woven sleeve.

16. The resector balloon system of claim 15, further comprising:
a central control system;
wherein the data collection system sends electrical impedance data to the central control system; and
wherein the central control system determines the distension of the woven sleeve based at least in part on the impedance data, and determines the diameter and dimensional characteristics of the balloon based at least in part on the determined distension.

17. The resector balloon system of claim 16, further comprising:
a user interface in communication with the central control system;
wherein the central control system sends a signal reflecting the determined diameter to the user interface.

18. The resector balloon of claim 16, further comprising:
a catheter coupled to the resector balloon;
a fluid source that inflates the resector balloon by supplying fluid thereto through the catheter; and
a fluid control system that controls the fluid source;
wherein:
the central control system sends a signal reflecting the determined diameter to the fluid control system; and
the fluid control system controls the fluid source based at least in part on the signal.

19. The resector balloon system of claim 14, wherein the data collection system obtains the electrical impedance of material in contact with the woven sleeve.

20. The resector balloon system of claim 19, further comprising:
a central control system;
wherein the data collection system sends impedance data to the central control system; and
the central control system determines a tissue type corresponding to the material in contact with the woven sleeve.

21. The resector balloon system of claim 20, wherein the central control system determines the tissue type by comparing the impedance data to a lookup table.

22. The resector balloon system of claim 20, further comprising:
a catheter coupled to the resector balloon;
fluid source that inflates the resector balloon by supplying fluid thereto through the catheter; and
a fluid control system that controls the fluid source;
wherein the fluid control system controls the fluid source based at least in part on the tissue type.

23. The resector balloon system of claim 20, further comprising:
a user interface in communication with the central control system;
wherein the central control system sends a signal reflecting the tissue type to the user interface.

24. The resector balloon system of claim 19, further comprising:
a user interface;
wherein the data collection system transmits impedance data to the user interface.

25. The resector balloon of claim 14, further comprising:
a catheter coupled to the resector balloon; and
at least one wire molded into said catheter for electrically connecting the woven sleeve to the data collection system.

26. The resector balloon of claim 1, wherein the woven sleeve comprises yarn coated with electrically conductive material.

27. The resector balloon of claim 1, wherein the woven sleeve comprises yarn coated with electrically insulative material.

28. The resector balloon of claim 1, wherein the woven sleeve comprises yarn that is alternately electrically insulative and conductive along its length.

29. The resector balloon of claim 1, wherein at least part of the woven sleeve is radio opaque.

30. The resector balloon of claim 1, further comprising:
a catheter coupled to the resector balloon;
wherein a proximal end and a distal end of the woven sleeve are coupled to a catheter.

31. The resector balloon of claim 30, wherein the proximal end and the distal end of the woven sleeve are glued, clamped, tied or otherwise affixed to the catheter.

32. The resector balloon system of claim 1, further comprising:
a catheter coupled to the resector balloon; and
a fluid source that inflates the resector balloon by supplying fluid thereto through the catheter.

33. A resector balloon system, comprising:
an inner balloon;
a woven sleeve comprising at least one woven thread and crossover points where the woven thread intersects in a weaving pattern, wherein the woven sleeve is disposed on at least a portion of the inner balloon;
an outer balloon comprising an outer wall having openings therein, wherein the inner balloon and the woven sleeve are disposed in the outer balloon, wherein the outer balloon forms a space between the inner balloon and the outer balloon, and wherein the outer wall comprises a resecting surface that resects biological material; and
knots located at the crossover points that at least partially extend through the openings in the outer balloon.

34. The resector balloon system of claim 33, wherein the inner balloon is mounted to a catheter with at least one of its proximal and distal ends turned inward and the outer balloon is mounted to the catheter with at least one of its proximal and distal ends turned outward.

35. The resector balloon system of claim 33, further comprising:
a catheter comprising a catheter lumen in fluid communication with the space between the inner balloon and the outer balloon.

36. The resector balloon system of claim 35, further comprising:
a fluid source in fluid communication with the catheter lumen that provides fluid to the space between inner balloon and the outer balloon; and
a control system that controls the fluid source, wherein the control system controls the distance that the knots extend through the openings in the outer balloon by controlling the amount of fluid the fluid source provides to the space between the inner balloon and the outer balloon.

37. The resector balloon of claim 33, wherein the woven sleeve is weft knit.

38. The resector balloon of claim 33, wherein the at least one woven thread is elastic string.

39. The resector balloon of claim 33, wherein the at least one woven thread is polyurethane string.

40. The resector balloon of claim 33, wherein the at least one woven thread comprises metallic fibers.

41. The resector balloon of claim 40, wherein the at least one woven thread comprises steel fibers.

42. The resector balloon of claim 33, wherein the woven sleeve comprises at least one electrically conductive thread.

43. The resector balloon of claim 42, wherein the electrically conductive threads comprise an electrically conductive core and an electrically insulative sheath.

44. The resector balloon of claim 42, wherein the electrically conductive threads comprise an electrically insulative core and an electrically conductive sheath.

45. The resector balloon of claim 42, wherein a proximal portion and a distal portion of the woven sleeve comprise electrically conductive threads and a middle portion of the woven sleeve comprises electrically insulative threads.

46. The resector balloon of claim 33, wherein the resector balloon is coupled to a catheter and a proximal end and a distal end of the woven sleeve are coupled to a catheter.

47. The resector balloon of claim 46, wherein the proximal end and the distal end of the woven sleeve are glued, clamped or otherwise affixed to the catheter.

* * * * *